United States Patent [19]
Bryce et al.

[11] Patent Number: 5,811,414
[45] Date of Patent: Sep. 22, 1998

[54] VITAMIN D3 ANALOGS USEFUL FOR REVERSING THE PHOTODAMAGE IN SUN-EXPOSED SKIN

[75] Inventors: Graeme Findlay Bryce; Milan Radoje Uskokovic, both of Upper Montclair, N.J.

[73] Assignee: Hoffmann-La Roche Inc., Nutley, N.J.

[21] Appl. No.: 857,839

[22] Filed: May 16, 1997

[51] Int. Cl.$^6$ .................................................. A61K 31/59
[52] U.S. Cl. ............................................................ 514/167
[58] Field of Search ............................................ 514/167

[56] References Cited

U.S. PATENT DOCUMENTS

| | | |
|---|---|---|
| 4,603,146 | 7/1986 | Kligman . |
| 5,087,619 | 2/1992 | Baggiolini et al. ..................... 514/167 |

OTHER PUBLICATIONS

Chemical Abstracts vol. 102: 119659m (Dikstein et al.) 1985.
The Merck Manual 16th ed. p. 2499 1992.
Kligman, et al., J. Invest. Dermatol. 78:181–189 (1982).
Johnston, et al. J. Invest. Dermatol 82:587–590 (1984).
Kligman, et al., Conn. Tissue Res. 12;139–150 (1984).

*Primary Examiner*—Leonard Schenkman
*Attorney, Agent, or Firm*—George W. Johnston; Patricia S. Rocha-Tramaloni; Robert A. Silverman

[57] ABSTRACT

The use of compounds of formula I as topical agents to combat the disorders of the skin, produced by photodamage, which disorders include wrinkling, elastosis and premature aging is described. Compounds of formula I are

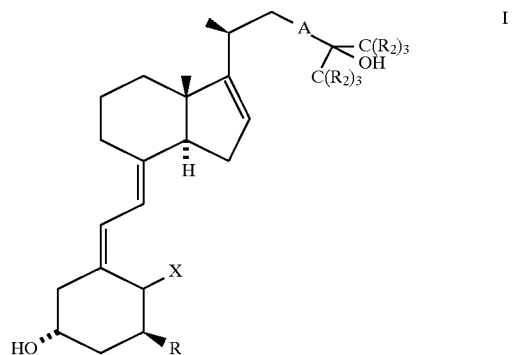

wherein R is hydrogen, fluorine, or hydroxy, $R_2$ is hydrogen, lower alkyl or halogen, X is =$CH_2$ or when R is hydroxy X is hydrogen or =$CH_2$,

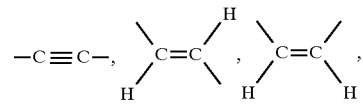

—$CH_2$—$CH_2$—, provided that when A is —$CH_2$—$CH_2$—, $R_2$ is hydrogen or lower alkyl.

12 Claims, No Drawings

VITAMIN D3 ANALOGS USEFUL FOR REVERSING THE PHOTODAMAGE IN SUN-EXPOSED SKIN

BACKGROUND OF THE INVENTION

The skin, particularly in humans, contains an elaborate network of elastin fibers which are responsible for maintaining its elastic properties. With excessive exposure to sunlight the elastic fiber system becomes hyperplastic, disorganized and ultimately disrupted. This is known as actinic elastosis and is the principal cause of wrinkling, discoloration and laxity of the skin in the exposed areas of the body. The skin can repair itself to some extent but it is nevertheless desirable to have an agent which can accelerate the repair of this prematurely aged skin.

The UVB irradiated hairless mouse has been found to be a convenient model for actinic elastosis in the skin. (Kligman et al. J. Invest. Dermatol. 78:181 (1982). It has been shown by Johnston et al. in J. Invest. Dermatol. 82:587 (1984) that irradiation with low levels of UVB which simulate realistic solar exposure leads to a significant increase in skin elastin as measured by desmosine content. The amount of this amino acid, which is isolated from acid hydrolysis of elastin, is proportional to the elastin present in the skin. (Uitto et al., Lab. Invest. 49:1216 (1973). Treatment of irradiated mice with topical retinoic acid has been shown to normalize the histological features of the skin in which the previously elastoic dermis has the appearance of unirradiated tissue (Kligman et al., Conn. Tissue Res. 12:139 (1984), Kligman U.S. Pat. No. 4,603,146 July 1986). Therefore, this model can be used to determine the efficacy of compounds in the repair of sun damaged skin.

SUMMARY OF THE INVENTION

The invention relates to compounds of the formula

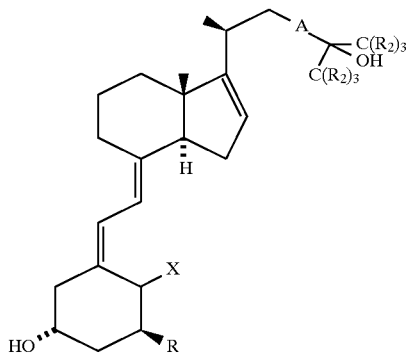

wherein R is hydrogen, fluorine, or hydroxy, $R_2$ is hydrogen, lower alkyl or halogen, X is $=CH_2$ or when R is hydroxy X is hydrogen or $=CH_2$,

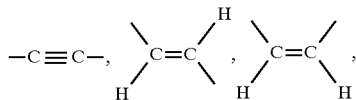

—$CH_2$—$CH_2$—, provided that when A is —$CH_2$—$CH_2$—, $R_2$ is hydrogen or lower alkyl which applied topically to the skin of a patient reverse the conditions associated with photodamage. Hence, by the topical application of compounds of formula I to the skin of patients which has been damaged through sun exposure, the effects of wrinkling, elastosis and premature aging can be reversed leading to an improvement in the appearance of the skin.

Through the topical administration of the compounds of the formula I, the acceleration of repair of dermal damage is accomplished so as to provide the skin with a smoother and younger appearance.

DETAILED DESCRIPTION OF THE INVENTION

The term "lower alkyl" as used herein denotes groups which preferably contain 1–4 carbon atoms. Alkyl groups can be straight-chain or branched-chain, such as, for example, methyl, ethyl, propyl, butyl, isopropyl and the like. Preferred lower-alkyl groups are methyl or ethyl. The term "halogen" embraces fluorine, chlorine, bromine and iodine, of which fluorine is preferred.

In the formulas presented herein, the various substituents are illustrated as joined to the nucleus by one of the following notations: a wedged solid line (◆) indicating a substituent which is above the plane of the molecule, (β-orientation) and a wedged dotted line (⋯⋯) indicating a substituent which is below the plane of the molecule (α-orientation).

The invention relates to compounds of the formula

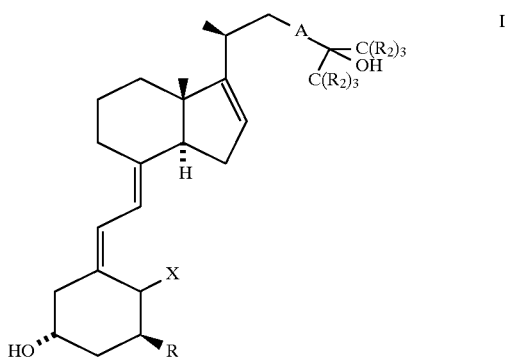

wherein R is hydrogen, fluorine, or hydroxy, $R_2$ is hydrogen, lower alkyl or halogen, X is $=CH_2$ or when R is hydroxy X is hydrogen or $=CH_2$,

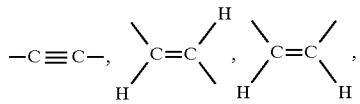

—$CH_2$—$CH_2$—, provided that when A is —$CH_2$—$CH_2$—, $R_2$ is hydrogen or lower alkyl which applied topically to the skin of a patient reverse the conditions associated with photodamage. Hence, by the topical application of compounds of formula I to the skin of patients which has been damaged through sun exposure, the effects of wrinkling, elastosis and premature aging can be reversed leading to an improvement in the appearance of the skin.

Of the compounds of formula I, there are preferred compounds wherein R is hydroxy. Further, preferred compounds of formula I are those in which $R_2$ is fluorine. Preferably, A is

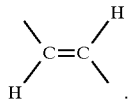

The following compound of formula I is especially preferred: 1,25-dihydroxy-16,23E-diene-26,27-hexalfuoro-20-epi-cholecalciferol.

Processes for preparing compounds of formula I, are set forth in copending U.S. Pat. application Ser. No. 08/857,544, filed May 16, 1997 concurrently herewith.

The compounds of formula I when applied topically to the skin, reverse the condition associated with photodamage so as to moderate and retard the damage to the skin caused by sun exposure. The damage caused sun exposure may include premature aging, elastosis and wrinkling. This damage is more pronounced in older patients. By applying the compounds of formula I topically to the skin in an amount effective to reverse the conditions associated with photodamage, the acceleration of skin repair is accomplished to enhance the skin with a smoother and younger appearance. The compounds of formula I should be applied to that portion or area of the skin which is affected by photodamage or in which treatment is desired. The use of the compounds of formula I in accordance with this invention can provide the effects of anti-aging and anti-wrinkling, as well as enhance the repair of sun damaged skin.

A compound of formula I, or a combination of compounds of formula I can be applied in accordance with this invention to human skin in conventional topical compositions. These compositions can be utilized to apply compounds of formula I to the skin of the body, particularly the face, legs, arms and hands. The preferred method of application of compounds of formula I topically to produce the best effects should start where a patient is between 30 and 55 years of age, when elastosis begins to appear and becomes more pronounced. Thereafter, this composition can be continuously applied to patients to reduce the effects and injury associated with sun exposure. Generally, it is preferred to begin the treatment when the patient reaches approximately 30 years of age and to continue the treatment throughout his life, in order that the effects of elastosis be reduced and to prevent any further progression of photodamage.

The compounds of formula I can be administered in accordance with this invention in any conventional suitable topical preparation, that is, in combination with any suitable conventional carrier useful for topical administration. Therefore, compounds of formula I can be administered in accordance with this invention in any suitable topical composition such as a cream, ointment, soap, solution, lotion, emulsion, shampoo, and the like. Generally, for most efficacious results, these topical compositions contain from about .00001% to about .1% by weight of the total composition of a compound of formula I, with amounts of from about .0001% to about .01% by weight of the composition being especially preferred. If desired, higher concentrations may be utilized depending upon the nature and extent of elastosis.

In formulating these compositions, any conventional non-toxic, dermatologically acceptable base or carrier in which a compound of formula I is stable can be utilized. The preferred compositions for use in this invention are the conventionally cosmetic compositions which can contain a cosmetically active ingredient which is topically administered to human skin to provide a cosmetic effect. Among the conventional cosmetically active materials which can be utilized in this composition are included: sunscreens, penetration enhancers, moisturizers, surfactants, emollient, colorants, conditioners, bacteriocides, astringents, detergents, and the like. The topical compositions of this invention can, if desired, contain suitable sunscreen agents. Any conventional sunscreen agent can be utilized in formulating the formulations containing compounds of formula I which can be utilized in accordance with this invention.

These topical compositions which contain compounds of formula I can contain any of the conventional excipients and additives commonly used in preparing topical compositions. Among the conventional additives or excipients, which can be utilized in preparing these cosmetic compositions in accordance with this invention are preservatives, thickeners, perfumes and the like. In addition, the conventional antioxidants, such as butylated hydroxyanisoles (BHA), ascorbyl palmitate, propyl gallate, citric acid, butylated hydroxy toluene (BHT), ethoxyquin, tocopherol, and the like can be incorporated into these compositions. These topical compositions can contain conventional acceptable carriers for topical applications which are generally utilized in these compositions. These compositions may contain thickening agents, humectants, emulsifying agents and viscosity stabilizers, such as those generally utilized. In addition, these compositions can contain flavoring agents, colorants, and perfume which are conventional in preparing cosmetic compositions.

The topical compositions containing compounds of formula I can be applied to the skin and should be preferably applied once daily to the skin. For obtaining the reversal of the elastosis so as to impart to the skin a smooth and younger appearance, the topical compositions should be preferably applied for a period of 6 months. After that, compositions which contain compounds of formula I should be applied continually to maintain the effect of younger and smoother skin. These preparations can be applied according to the need of the patient as determined by the prescribing physician. In any event, the particular regimen for application of this composition to a patient will typically depend on the age, weight and skin condition of the individual.

The invention is further illustrated in the following examples. These examples are for illustration and are not limitive of the claimed invention.

EXAMPLE 1

Repair of UVB-Induced Dermal Damage in the Hairless Mouse by Compounds of Formula I Hairless mice (female, HRS/J strain, Jackson Labs, 5–7 weeks old at the start of the experiments) were housed in yellow light and irradiated three times per week with a bank of 8 Westinghouse Sunlamps (FS72T12 HO, peak irradiance at 313 nm) placed about 20 cm above the animals. UVB output was measured on an International Light Research Radiometer, model IL 1700, using a SEE240 detector. With this setup, the lamp output was approximately 3.5 mW/cm$^2$ and the time of exposure for 0.06 J/cm$^2$ was about 17 seconds; 1 MED is approximately 0.03 J/cm$^2$. The precise dose was delivered by a IL 844A Phototherapy Exposure Control. Daily doses were 0.03 J/cm$^2$ for two weeks, 0.06 J/cm$^2$ for two weeks and 0.08 J/cm$^2$ thereafter, until a total dose of approximately 4 j/cm$^2$ was accumulated. To effect repair of the dermal damage, the UVB irradiation was discontinued and the animals were divided into groups of approximately eight and treated three times per week with various concentrations of the vitamin D analogs dissolved in ethanol. All dosing was done under yellow light. A control group treated with acetone alone was included. Two-cm strips of dorsal skin were taken longitudinally down the center of the irradiated (and treated) area. Elastin fibers were stained with Luna's aldehyde fuchsin and collagen by Van Gieson. In this model, repair is defined by the appearance of a normalized dermis extending from the epidermis down to the layer of compressed elastin. The extent of repair is reflected by the width of this zone. In these studies, since the width of the zone varies considerably, the area of the zone on a standard length of histological section is measured by image analysis. Compounds are tested at three doses and an approximate $ED_{50}$ calculated.

The results are given in Table I.

TABLE I

| Compound | Dose ($\mu$g) | Repair Zone mm$^2$ |
|---|---|---|
| Control | | 0.0028 ± 0.0008 |
| Compound A | 0.1 | 0.0282 ± 0.0092*** |
| | 0.5 | 0.0102 ± 0.0067* |

*P < 0.05, P < 0.01, *P < 0.001 vs vehicle control

Throughout the specification, Compound A is 1,25-dihydroxy-16,23E-diene-26,27-hexafluoro-20-epi-cholecalciferol.

Creams, gels and solutions containing ingredients within the proportions set forth in Examples II through IV below, can be formulated by conventional means. Reference to Compound A in the Examples is illustrative of any of the claimed compounds.

EXAMPLE II

Cream

| Ingredients | % w/w |
|---|---|
| Compound A | 0.00001–0.10 |
| Cetyl Alcohol | 1.50 |
| Stearyl Alcohol | 2.50 |
| Sorbjtan Monostearate (Span 60) | 2.00 |
| Mineral Oil | 2.00 |
| Glyceryl Monostearate and Polyoxy-ethylene Glycol Stearate Blend (Arlacel 165) | 4.00 |
| Polysorbate 60 (Tween 60) | 1.00 |
| Caprylic/Capric Triglyceride | 5.00 |
| Sorbitol Solution | 4.00 |
| Edetate Disodium | 0.10 |
| Butylated Hydroxyanisole (BHA) | 0.02 |
| Sorbic Acid | 0.20 |
| Potassium Sorbate | 0.1–0.2 |
| Water q.s. to | 100.00 |

Procedure for Cream

1. In a stainless steel container, dissolve drug in caprylic/capric triglyceride while stirring.

2. In a separate stainless steel container melt cetyl alcohol, stearyl alcohol, span 60, mineral oil, arlacel 165, tween 60 and BHA at 70–75° C.

3. Add the drug solution from Step 1 to the oily solution from Step 2 while mixing.

4. In an appropriate container heat water, sorbitol solution, edetate disodium, sorbic acid and potassium sorbate to 70–75° C.

5. Add the solution from Step 3 to the solution from Step 4 while emulsifying with a high speed mixer.

6. Cool the emulsion from Step 5 to room temperature until congels.

EXAMPLE III

Gel

| Ingredients | % w/w |
|---|---|
| Compound A | 0.00001–0.10 |
| Butylated Hydroxyanisole (BHA) | 0.02 |
| Hydroxypropyl Cellulose | 3.00 |
| Ethyl Alcohol, USP | 45.00 |
| Water q.s. to | 100.00 |

Procedure for Gel

1. In a stainless steel container dissolve BHA in ethyl alcohol and water mixture.

2. Dissolve drug in the solution from Step 1.

3. Disperse hydroxypropyl cellulose in the solution from Step 2.

EXAMPLE IV

| Ingredients | % w/w |
|---|---|
| Compound A | 0.00001–0.10 |
| Propylene Glycol | 10.00 |
| Caprylic/Capric Triglyceride | 30.00 |
| Butylated Hydroxyanisole (BHA) | 0.02 |
| Ethyl Alcohol, Absolute q.s. to | 100.00 |

Procedure for Topical Solution

1. In a stainless steel container dissolve drug in ethyl alcohol.

2. Add and dissolve BHA to the solution from Step 1.

3. Add propylene glycol and caprylic/capric triglyceride to the solution from Step 2 and mix until solution becomes clear.

We claim:

1. A method of treating the conditions associated with photodamaged skin comprising topically administering a compound of the formula

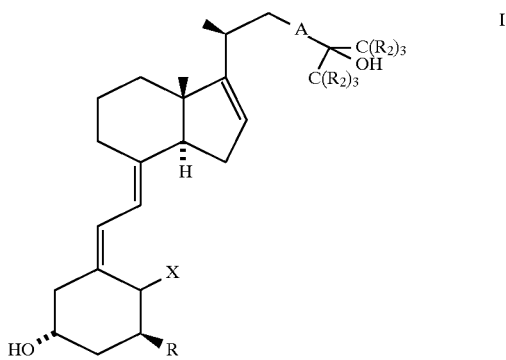

wherein R is hydrogen, fluorine, or hydroxy, $R_2$ is hydrogen, lower alkyl or halogen, X is $=CH_2$ or when R is hydroxy X is hydrogen or $=CH_2$,

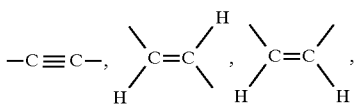

—CH$_2$—CH$_2$—, provided that when A is —CH$_2$—CH$_2$—, R$_2$ is hydrogen or lower alkyl to an area of skin in need of said treatment, said compound of formula I being applied to said area in an amount effective to reverse the effects of photodamage in said area.

2. A method according to claim 1, wherein in the compound of formula I, A is

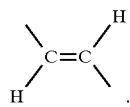

3. A method according to claim 1, wherein in the compound of formula I, R$_2$ is hydroxy.

4. A method according to claim 1, wherein in the compound of formula I, R$_2$ is fluorine.

5. A method according to claim 1, wherein the compound of formula I is 1,25-dihydroxy-16,23E-diene-26,27-hexafluoro-20-epi-cholecalciferol.

6. The method of claim 1, wherein the compound of formula I is administered in a topical composition containing at least .00001% by weight of said compound of formula I and an inert dermatologically acceptable carrier.

7. The method of claim 6, wherein said topical composition contains a compound of formula I in an amount of from about .00001% to about .1% by weight of the composition.

8. The method of claim 7, wherein said topical composition contains a compound of formula I in an amount of from about .0001% to about .01% by weight of the composition.

9. The method of claim 8, wherein said composition contains a cosmetically active ingredient.

10. The method of claim 9, wherein said cosmetically active ingredient is a sunscreen.

11. The method of claim 6, wherein said composition is a gel, cream or ointment.

12. The method of claim 6, wherein said composition is applied to the face.

* * * * *